(12) United States Patent
Alby

(10) Patent No.: US 6,387,097 B1
(45) Date of Patent: May 14, 2002

(54) IMPLANT FOR OSTEOSYNTHESIS DEVICE WITH HOOK

(75) Inventor: Albert Alby, Ch-Essertines (CH)

(73) Assignee: Scient'x Societe a Responsabilite Limitee, Paris (FR)

( * ) Notice: Subject to any disclaimer, the term of this patent is extended or adjusted under 35 U.S.C. 154(b) by 0 days.

(21) Appl. No.: 09/423,310

(22) PCT Filed: May 15, 1998

(86) PCT No.: PCT/FR98/00979

§ 371 Date: Feb. 14, 2000

§ 102(e) Date: Feb. 14, 2000

(87) PCT Pub. No.: WO98/52483

PCT Pub. Date: Nov. 26, 1998

(30) Foreign Application Priority Data

May 16, 1997 (FR) .............................................. 97 06027

(51) Int. Cl.$^7$ .............................................. A61B 17/70
(52) U.S. Cl. ...................................................... 606/61
(58) Field of Search ........................................... 606/61

(56) References Cited

U.S. PATENT DOCUMENTS

| | | | |
|---|---|---|---|
| 5,643,262 A | * | 7/1997 | Metz-Stavenhagen et al. ... 606/61 |
| 5,667,508 A | * | 9/1997 | Errico et al. ................... 606/61 |
| 5,702,393 A | * | 12/1997 | Pfaifer ........................ 606/61 |
| 5,725,527 A | * | 3/1998 | Biedermann et al. ......... 606/61 |
| 5,947,967 A | * | 9/1999 | Barker ........................ 606/61 |
| 6,077,263 A | * | 6/2000 | Ameil et al. ................... 606/61 |
| 6,117,136 A | * | 9/2000 | Von Strempel .............. 606/61 |
| 6,136,000 A | * | 10/2000 | Louis et al. ................... 606/61 |

* cited by examiner

Primary Examiner—Paul J. Hirsch
(74) Attorney, Agent, or Firm—Bacon & Thomas, PLLC

(57) ABSTRACT

A spinal implant device arranged to clamp at least one vertebra includes a link rod, a hook defining a central bore and secured to a fixing head, a counterhook, an elongate member, a position control device and an interconnection arrangement between the counterhook and the hook. The fixing head has a pair of upwardly extending members forming a channel configured to accommodate the link rod. A nut engages the fixing head to exert a downward force onto the link rod. The elongate member attaches at one end to the counterhook and slidably engages the central bore of the hook such that the hook and the counterhook cooperate to define a clamp. The position control device cooperates with the hook and the elongate member to selectively maintain the hook in a position relative to the counterhook.

12 Claims, 4 Drawing Sheets

IMPLANT FOR OSTEOSYNTHESIS DEVICE WITH HOOK

TECHNICAL FIELD

The present invention relates to an implant for an osteosynthesis device, in particular for the spine, the implant comprising a bone-anchoring device surmounted by a fixing head constituted by two upwardly extending members or lateral branches forming an open U-shaped channel and designed to receive a link rod in order to hold it in place by clamping, via a tapped nut suitable for being screwed onto corresponding threaded portions made on the walls of the lateral branches of the fixing head.

PRIOR ART

It is generally known to use hooks or pedicular screws as bone-anchoring devices. Numerous devices relate to pedicular screws which have the advantage of providing effective fixing for the implant since a pedicular screw is anchored by being screwed into a pedicle.

Nevertheless, it is not always possible to use pedicular screws, particularly for a vertebra at the end of the spine, or because of regulations in certain countries which allow pedicular screws to be used only under very restrictive circumstances, use thereof being considered difficult and therefore dangerous for the patient.

Thus, in some cases, it is necessary to make use of hooks.

The hooks that are normally used are shaped so as to hook onto a projecting portion of the bones of the spine, such as the foot of a pedicle, or else to fix on the vertebral arch, either on the infralamary side or on the supralamary side.

Nevertheless, it must be observed that using hooks gives rise to numerous drawbacks since a single hook cannot on its own provide effective mechanical fixing as can be done by a screw. Hooks can act effectively only as an abutment when used in association with another hook so as to obtain a clamping effect in which case it becomes almost as effective as a screw.

A hook comprises a hook body having an inner bearing face and an outer fixing face provided with means for fixing to a rod for interconnecting anchoring points. It is the interconnecting rod that serves to hold the hooks on two successive vertebrae.

Such an assembly has the effect of securing two successive vertebrae together by moving them towards each other, but it does not provide any means for acting on either of them separately. In addition, it is necessary to find correct bearing points for both hooks simultaneously, and lateral stabilization is insufficient.

Anchoring devices using hooks have already been proposed that include devices for improving stability. Thus, international patent application WO-A-91/01691 describes a device comprising two facing hooks situated on either side of the vertebra, interconnected by a clamping screw for moving them towards each other on request, each hook having a fixing head in which a rod for linking together and preventing relative movement of the assembly is engaged by clamping nuts on each of said hooks.

That embodiment suffers from the major drawback of requiring clamping action to be taken on two hooks and of relying on the link rod to obtain effective clamping, which amounts to saying that prior thereto, the device remains unstable.

The same clamp system is to be found in documents FR 2,695,550 or FR 2,718,994.

Also known, e.g. from patent FR 2,695,550, is a self-contained implant having its own effective fixing means so that it does not require the link rod whose purpose is to link together two or more successive vertebrae. That patent describes a pedicular clamp having a hook secured to a fixing head constituted by two lateral branches forming an open U-shaped channel and designed to receive a link rod in order to prevent it from moving relative thereto by means of a tapped nut suitable for screwing onto corresponding threaded portions made on the lateral branches of the fixing head. That implant also has a counterhook directed towards the said hook and connected thereto by means of an elongate member, finger or threaded rod. The hook and the counterhook are designed to clamp onto opposite sides of a vetrebra independently of the link rod.

That implant suffers from a major drawback relating to the possibility of relative movement between the hook and the counterhook. It also turns out that the operation of adjusting the spacing between the hook and the counterhook with that kind of implant is not an operation than is simple to carry out successfully.

SUMMARY OF THE INVENTION

The invention thus seeks to remedy the above-specified drawbacks by proposing an implant for an osteosynthesis device implementing a hook and a counterhook which are independent of the link rod and which offer the advantages firstly of making it easy to adjust the spacing between the hook and the counterhook, and also to maintain them in a relative position, and secondly of preventing the hook and the counterhook from moving relative to each other in a manner that is safe and effective.

The invention thus provides a solution serving firstly to provide primary stabilization of bone anchoring by means of hooks, by improving the bone anchoring as from the preliminary step of placing the implant on the spine, during the step of reducing deformation of the spine and throughout the subsequent duration of the spine being held in place, and secondly of providing the anchoring with stability that is reliable and permanent so as to avoid loss of reduction in the short or medium term.

To achieve this object, the implant comprises:

a hook secured to a fixing head constituted by two lateral branches in an open U-shaped channel designed to receive a link rod for the purpose of preventing movement relative thereto by means of a tapped nut suitable for being screwed onto corresponding threaded portions made on the lateral branches of the fixing head; and a counterhook directed towards the hook and freely connected to said hook to enable the hook and the counterhook to clamp onto at least one vertebra, independently of the link rod.

According to the invention, the implant includes:

an elongate member connected at one end to the counterhook and arranged to slide in a bore formed in the top potion of the hook and while lying substantially along a center plane of the hook;

a position control device for holding the hook and the counterhook in position relative to each other; and an interconnection arrangement between the hook and the counterhook preventing relative motion of the hook and counterhook.

Various other characteristics appear from the following description given with reference to the accompanying drawings which show embodiments and implementations of the invention as non-limiting examples.

BEST METHOD OF PERFORMING THE INVENTION

Figure 1:
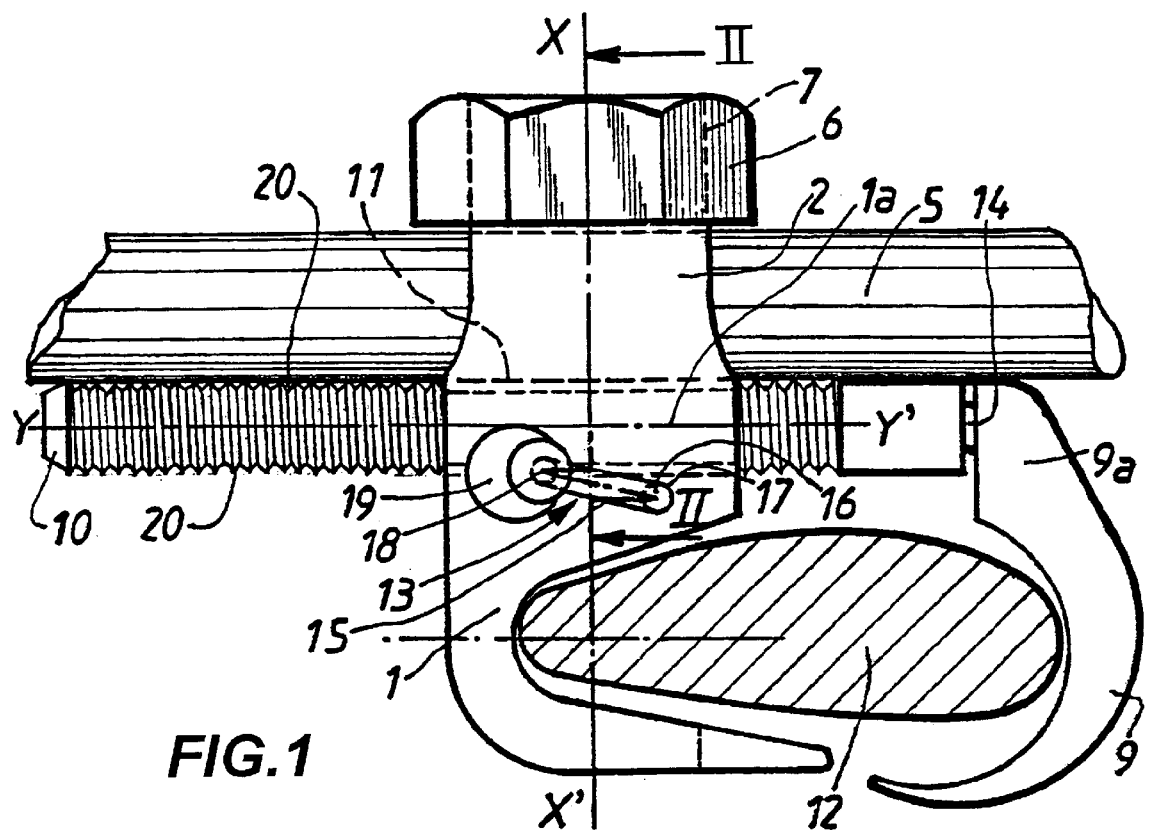
FIG. 1 is an elevation view of an embodiment of the invention.
Figure 2:
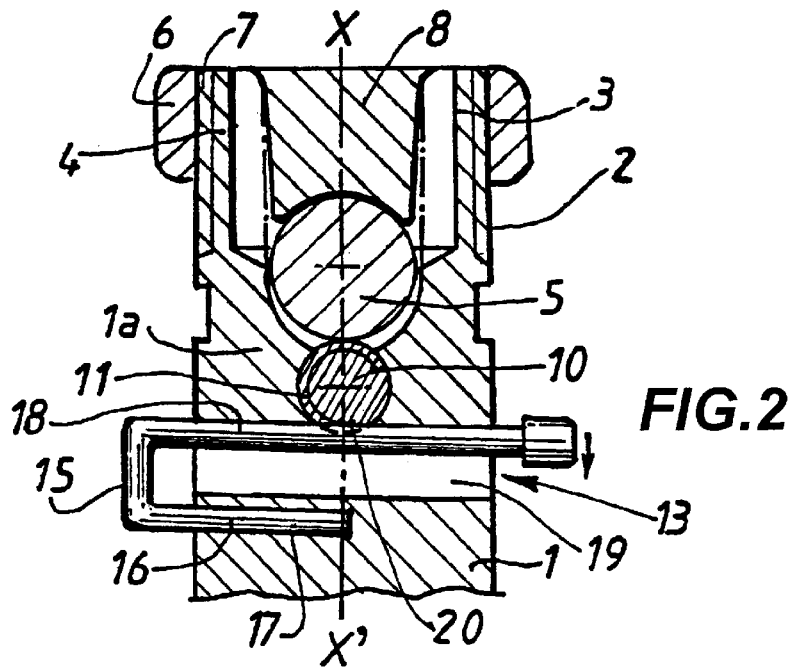
FIG. 2 is a section view of the top portion of the implant along line II—II of FIG. 1.

The implant shown in FIGS. 1 and 2 comprises a reference hook 1 and a counterhook 9. The hook 1 is secured to a fixing head 2 which is constituted in conventional manner by two upwardly extending members or lateral branches 3, 4 forming an open U-shaped channel and designed to receive between them a link rod 5, for the purpose of holding it fixed relative thereto by means of a tapped nut 6 suitable for being screwed onto corresponding threaded portions 7 made in the example shown on the outside walls forming portions of cylinders of the lateral branches 3, 4 of the fixing head 2.

In the embodiment shown in FIGS. 1 and 2, the nut 6 has a shoe 8 in its diametral zone, which shoe 8 is mounted so as to rotate freely and is designed to cooperate with the link rod 5 by clamping thereagainst.

The implant has free connection means between the hook 1 and the counterhook 9 enabling them to be moved freely towards each other or away from each other. The counterhook 9 faces towards the hook 1 and co-operates freely therewith by means of an elongate member or a finger 10. The finger 10 extends one of the ends 9a of the counterhook 9 and it slides in a central bore, a cylindrical hole, or a cylindrical drilling 11 formed in the top portion 1 a of the hook 1 and situated substantially in the same plane as the hook 1.

Thus, sliding of the finger 10 of the counterhook 9 in the bore 11 of the hook 1 enables the hook 1 and the counterhook 9 to clamp a vertebra 12 to a greater or lesser extent by acting on opposite sides of the vertebra 12, and to do so independently of the link rod 5. The assembly comprising the hook 1 and the counterhook 9 is held in place on the vertebra 12 by means 13 belonging thereto. The implant of the invention thus includes means 13 adapted to maintain the hook 1 in position relative to the counterhook 9.

As shown in FIGS. 1 and 2, the axis Y–Y' of the bore 11 in the hook 1 which receives the finger 10 of the counterhook 9, extends perpendicularly to the common vertical axis X–X' of the fixing head 2 and of the hook 1, and lies in a plane that is identical to the plane of the hook 1, thus putting the hook and the counterhook 9 face to face.

Figure 6:
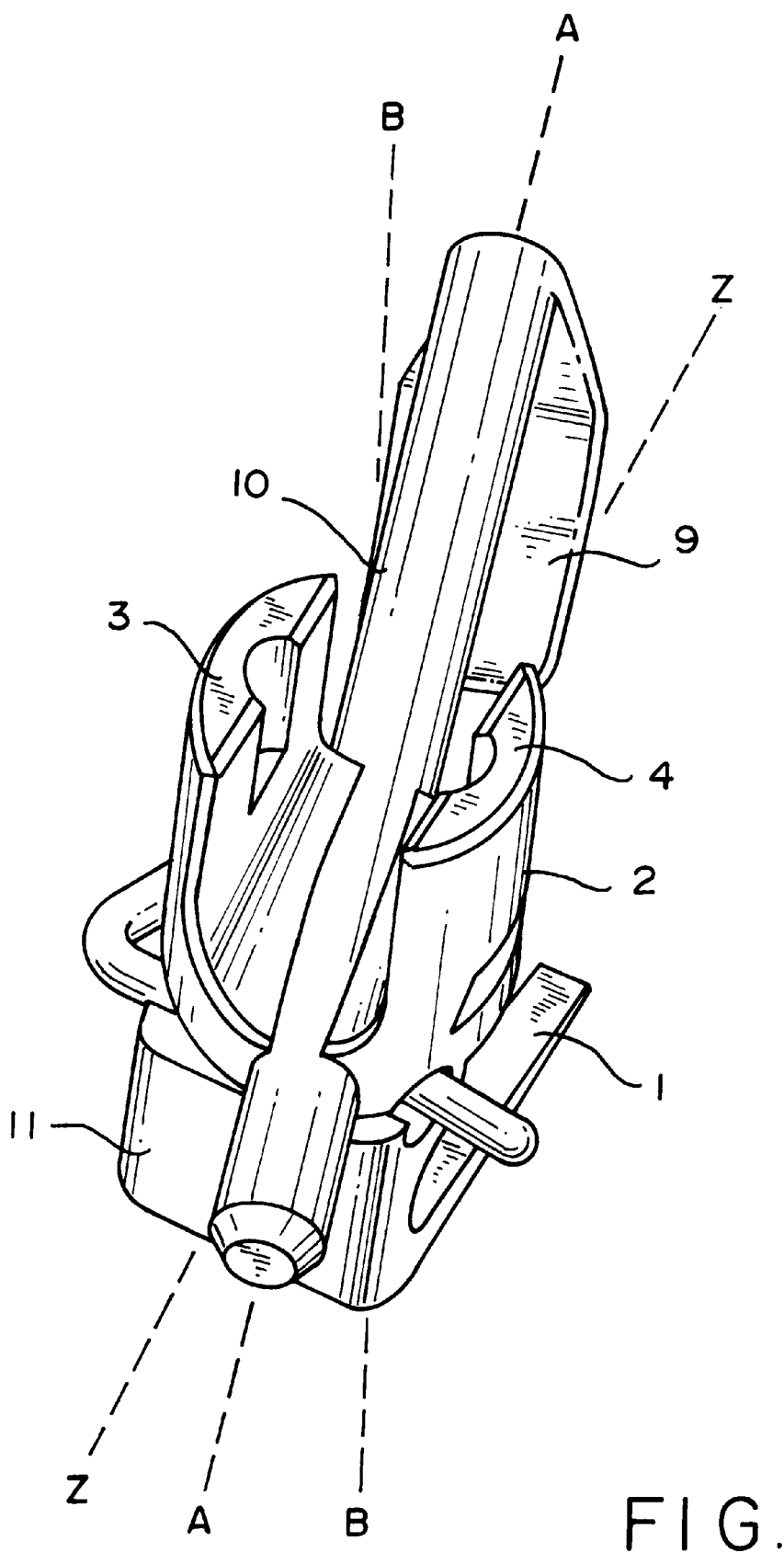
FIG 6. is a prespective view of another embodiment of the counterhook invention arranged obliquely to the hook.

In an alternative embodiment shown in FIG. 6, the longitudinal axis A—A of the central bore 11 is aligned perpendicular to the vertical axis B—B of the fixing head 2. However, the central longitudinal axis A—A of the central; bore 11 is aligned obliquely to the central longitudinal axis Z—Z of the hook 1 such that the counterhook 9 and the hook 1 are in a mutually offset relation to one another.

In another embodiment of the invention shown in FIG. 8, the counterhook 9 is pivotably connected to the finger 10, thereby enabling it to hinge relative to the axis Y–Y'.

In another embodiment of the invention, the fixing head 2 is rotatably mounted to the hook 1.

The means 13 for holding the hook 1 and the counterhook 9 in place are formed by an elastically deformable element constituted by a pin 15, in the example shown in FIGS. 1 and 2.

This pin has a branch 16 that is fixed in a housing 17 whose longitudinal axis extends substantially perpendicularly to the plane of the hook 1 in the top portion 1a thereof. The other branch 18 of the pin 15 is elastically deformable and is received freely in a cylindrical hole 19 that is substantially parallel to the first housing 17 and that is formed through the top portion 1a of the hook 1. The holes 11 and 19 intersect and they are substantially perpendicular. In this way, during clamping by moving the counterhook 9 towards the hook 1, the resilient branch 18 cooperates like a pawl with notches 20 formed along the finger 10, e.g. transversely, or else it can release the hooks by being lowered. It must be understood that the pin 15 allows the hook 1 and the counterhook 9 to move towards each other but prevents them from moving apart unless action is exerted specifically on the elastically deformable element which thus acts as a non-return system.

Figure 3:
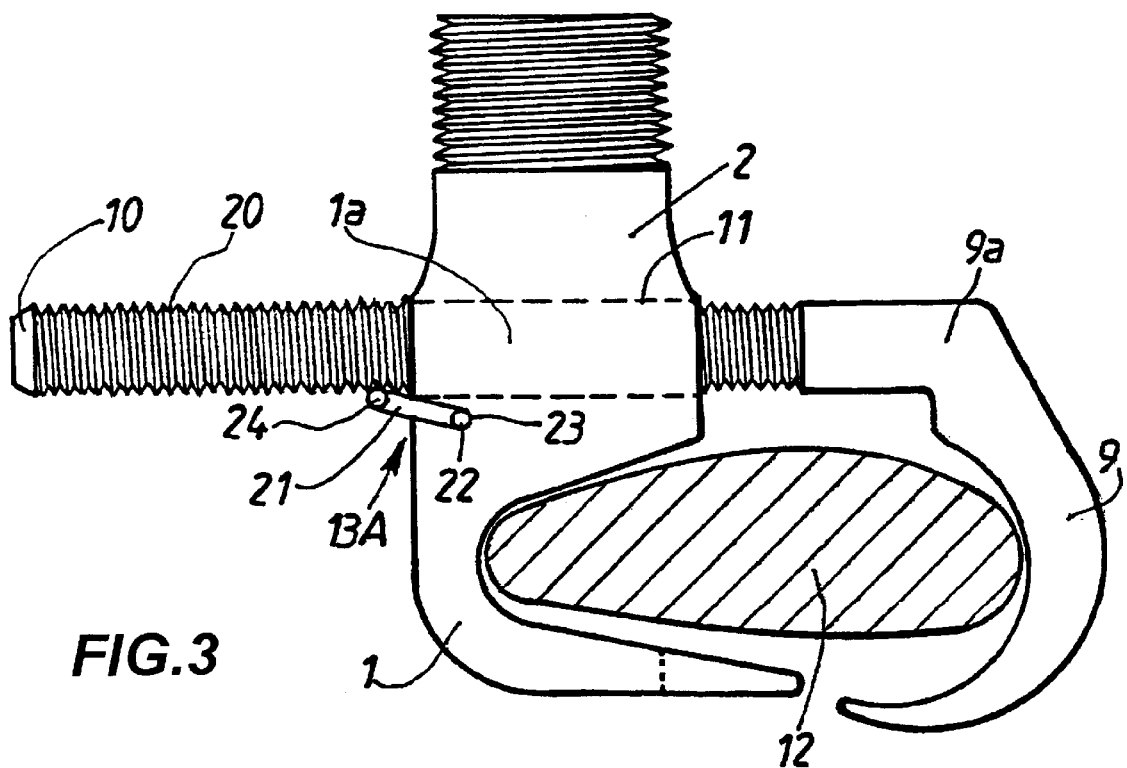
FIG. 3 is an elevation view of another embodiment of the invention from which the nut and the link rod are omitted.

In the embodiment shown in FIG. 3, the means (13A) for holding the hook 1 and the counterhook 9 in place on a given vertebra 12 are constituted by an elastically deformable element formed by a pin 21 having one branch 22 fixed in a housing 23 whose axis extends substantially perpendicularly to the plane of the hook 1 through the top portion 1a thereof; its other branch 24 is elastically deformable and extends freely and parallel to the first branch outside the hook 1 so as to co-operate with the finger 10 of the counterhook 9 which is substantially perpendicular thereto. In this way, during clamping in which the counterhook 9 is moved towards the hook 1, the resilient branch cooperates like a pawl with the notches 20 formed transversely on the finger 10, or it can release the finger on being moved down.

Figure 4:
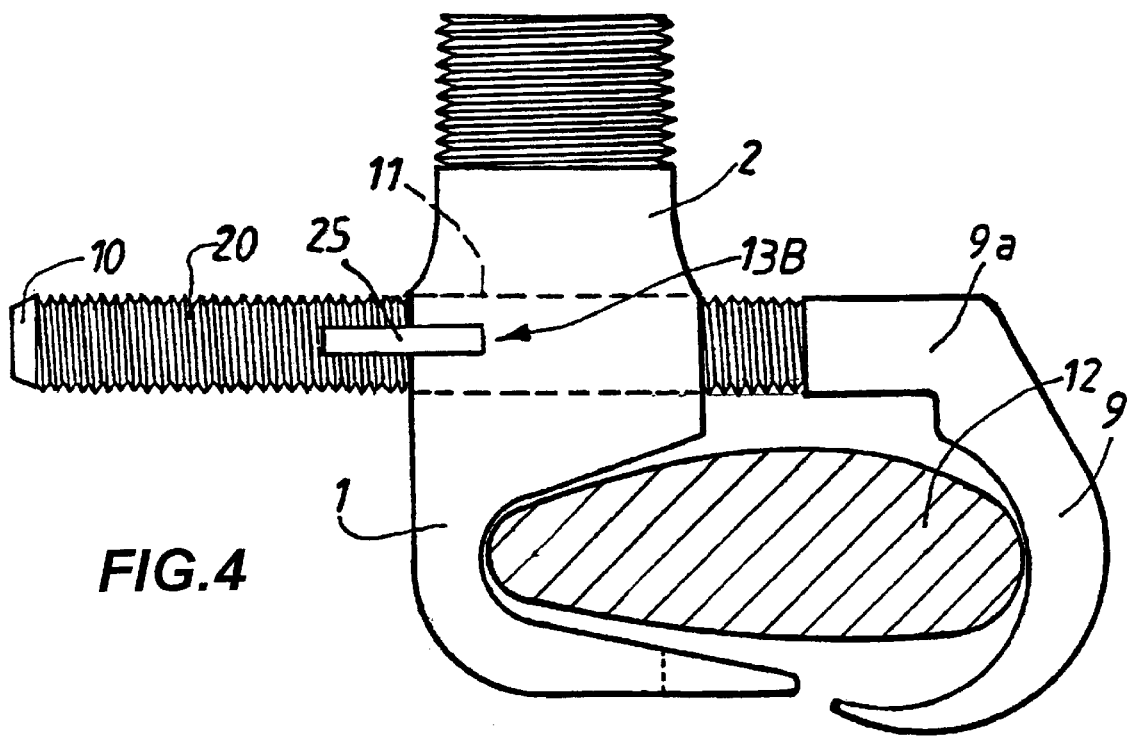
FIG. 4 is an elevation view of another embodiment of the invention from which the nut and the link rod are omitted.
Figure 5:
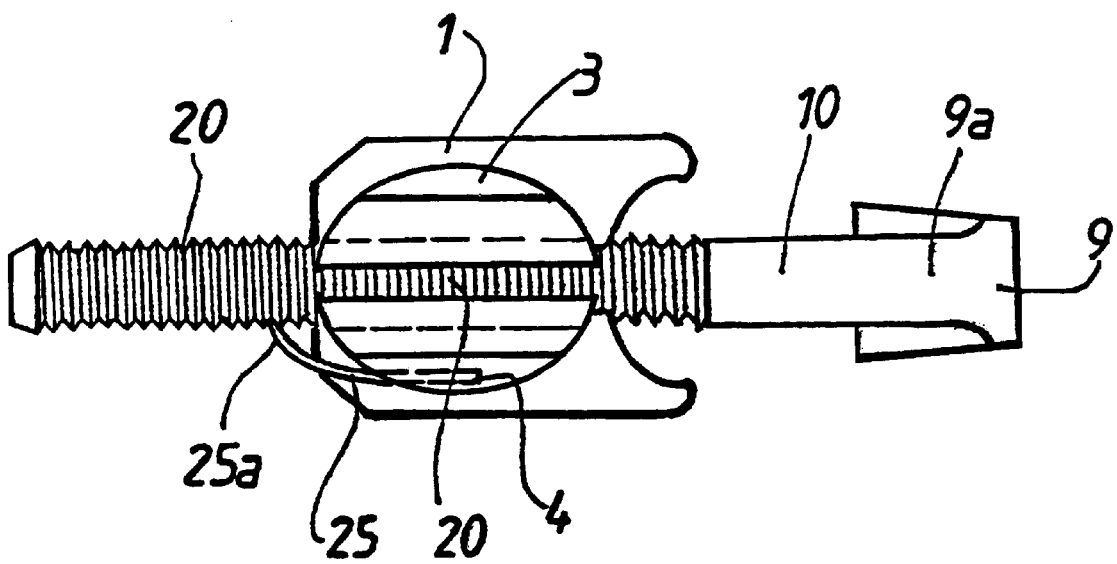
FIG. 5 is a view of the FIG. 4 embodiment seen from above.

In the embodiment shown in FIGS. 4 and 5, the means (13B) for holding the hook 1 and the counterhook 9 in place on a given vertebra 12 are constituted by an elastically deformable blade 25 fixed parallel to the plane of the hook 1, parallel to the finger 10 of the counterhook 9, and having its free end 25a curved towards the finger 10. In this way, during clamping by moving the counterhook 9 towards the hook 1, the free end 25 cooperates like a pawl with the notches 20 formed transversely along the finger 10, or else it can allow the finger to be released when traction is applied to the blade 25.

According to a characteristic common to all of the embodiments described above and visible in particular in FIG. 2, the implant has an interconnection arrangement locking the hook 1 and the counterhook 9 in a final position so as to ensure that they cannot move relative to each other. In a preferred embodiment of the invention, clamping the link rod 5 simultaneously causes the link rod to lock the finger 10. The bore 11 is made so as to intersect the bottom of the U-shape defined by the lateral branches 3 and 4 of the fixing head 2 for receiving the link rod 5 so that when said rod 5 is clamped by the nut 6 it simultaneously provides final clamping of said rod 5 and of the finger 10 relative to the hook 1. The hook 1 and the counterhook 9 are thus definitively prevented from moving relative to each other after previously being put into place and held in position with the help of the elastically deformable element.

In an alternative embodiment of the counterhook of the above-mentioned type, the counterhook can include a traditional pedicular screw so as to reinforce its fixing relative to a given vertebra.

It should be observed that the hook 1 and the counterhook 9 can be designed to clamp around a single vertebra or a plurality of vertebrae.

The implant of the invention thus makes it easy to adjust the spacing between the hook 1 and the counterhook 9 merely by moving the hook and the counterhook relative to each other so as to clamp onto one or more vertebrae. The hook 1 and the counterhook 9 are held in this stable position throughout the duration of the preliminary step of putting the implant into place and reducing the deformation of the spine. Definitive and reliable prevention of relative movement between the hook and the counterhook is performed during the later step of definitively fixing the implant.

What is claimed is:

1. A spinal implant device arranged to clamp at least one vertebra comprising:
    a link rod;
    a hook defining a central bore and securing to a fixing head, said fixing head having an external threaded portion and a pair of upwardly extending members delimiting between them a channel configured to accommodate said link rod;
    a nut configured and dimensioned to engage the external threaded portion of said upwardly extending members and exert an axial force against said fixing head to retain said link rod within said channel;
    a counterhook;
    an elongate member attached at one end to said counterhook and slidably engaging said central bore of said hook such that said hook and said counterhook cooperate to define a clamp independent of movement of said hook along said link rod;
    a position control device cooperating with said hook and said elongate member to selectively maintain said hook in a position relative to said counterhook; and
    an interconnection arrangement between said link rod and said elongate member preventing relative motion between said link rod and said elongate member.

2. The spinal implant device according to claim 1 wherein the position control device comprises an elastically deformable element supported by said hook and arranged to cooperate with a plurality of notches formed along said elongate member to secure said hook with said elongate member.

3. The spinal implant device according to claim 1 wherein the interconnection arrangement includes the link rod exerting a compressive force onto said elongate member when said nut is secured onto said fixing head.

4. The spinal implant according to claim 2 wherein said central bore intersects with said channel formed by said upwardly extending members such that said link rod exerts a compressive force onto said elongate member when said nut is secured onto said fixing head.

5. The spinal implant according to claim 1 wherein a longitudinal axis of said central bore is aligned perpendicular to a vertical central axis of said fixing head such that said hook and said counterhook are aligned along parallel vertical central axes such that said hook and said counterhook face each other in parallel relation.

6. The spinal implant according to claim 1 wherein a longitudinal axis of said central bore is aligned perpendicular to a vertical central axis of said fixing head and said longitudinal axis of said central bore is aligned obliquely to a horizontal central axis of said hook such that said hook and said counterhook face each other in an oblique, offset relation.

7. The spinal implant according to claim 1 wherein said counterhook is pivotably connected to said one end of said elongate member.

8. The spinal implant according to claim 1 wherein said fixing head is rotatably mounted onto said hook.

9. The spinal implant according to claim 2 wherein said elastically deformable element includes a pin having one branch extending into a recess formed by said hook which extends in a direction transverse relative to a longitudinal axis of said bore, and a resilient second branch extending into a cylindrical hole formed by said hook and intersecting a portion of said bore oppositely opposed to said channel of said fixing head, said second branch cooperating with said plurality of notches of said elongate member to operatively secure a position of said hook with respect to said counterhook.

10. The spinal implant according to claim 2 wherein said elastically deformable element includes a pin having one branch arranged to extend into a recess formed by said hook which extends in a direction transverse relative to a longitudinal axis of said bore, and a resilient second branch positioned outside of said hook and parallel to said first branch so as to cooperate with said plurality of notches of said elongate member to operatively secure a position of said hook with respect to said counterhook.

11. The spinal implant according to claim 2 wherein said elastically deformable element comprises an elastically deformable blade connected to said hook and arranged parallel to a longitudinal axis of said elongate member, said blade defining a free end directed towards said elongate member such that said free end operatively engages said plurality of notches of said elongate member to secure said hook in a position with respect to said counterhook.

12. The spinal implant according to claim 1 wherein the counter hook is arranged with a pedicular screw.

* * * * *